United States Patent [19]

Leeder

[11] 4,134,922

[45] Jan. 16, 1979

[54] ISOMERIZATION PROCESS

[75] Inventor: Geoffrey M. A. Leeder, Luton, England

[73] Assignee: Hoffmann-La Roche Inc., Nutley, N.J.

[21] Appl. No.: 836,877

[22] Filed: Sep. 26, 1977

[30] Foreign Application Priority Data

Oct. 14, 1976 [GB] United Kingdom ............... 42725/76

[51] Int. Cl.$^2$ ................................................. C07F 9/54
[52] U.S. Cl. ............................................... 260/606.5 F
[58] Field of Search .................................. 260/606.5 F

[56] References Cited

U.S. PATENT DOCUMENTS 3,600,473  8/1971  Surmatis ....................... 260/606.5 P

FOREIGN PATENT DOCUMENTS 843422  8/1960  United Kingdom ............. 260/606.5 F
1391806  4/1975  United Kingdom ............. 260/606.5 F

*Primary Examiner*—Helen M. S. Sneed
*Attorney, Agent, or Firm*—Jon S. Saxe; Bernard S. Leon; William H. Epstein

[57] ABSTRACT

A process for isomerizing a 9-cis-beta-ionylidenethyltriarylphosphonium salt to the corresponding 9-trans-beta-ionylidenethyltriarylphosphonium salt.

12 Claims, No Drawings

ISOMERIZATION PROCESS

SUMMARY OF INVENTION

The present invention relates to an isomerization process. More particularly, the invention is concerned with a process for the isomerization of a 9-cis-beta-ionylidenethyltriarylphosphonium salt of the formula

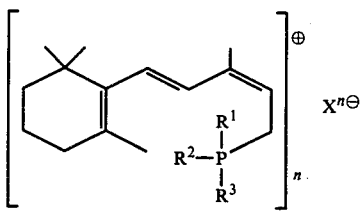

wherein $R^1$, $R^2$ and $R^3$ are aryl; $X^{n\ominus}$ is an anion of a strong acid; and n is 1, 2 or 3,
to a corresponding 9-trans-beta-ionylidenethyltriarylphosphonium salt of the formula

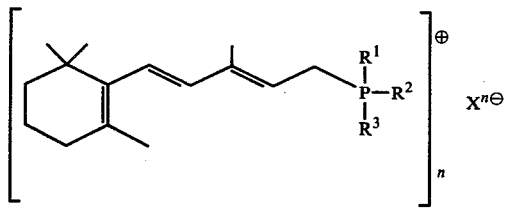

wherein n, $R^1$, $R^2$, $R^3$ and $X^{n\ominus}$ are as above,
which process comprises heating said 9-cis-beta-ionylidenethyltriarylphosphonium salt in the presence of an organic solvent.

DETAILED DESCRIPTION

The aryl groups denoted by $R^1$, $R^2$ and $R^3$ in the foregoing formula can be any conventional aryl groups. The term aryl includes mononuclear aromatic hydrocarbon groups such as phenyl, which can be unsubstituted or substituted in one or more positions with halogen, nitro, lower alkyl, or lower alkoxy substituents as well as polynuclear aryl groups such as naphthyl or anthryl which can be unsubstituted or substituted with any of the aforementioned substituents. Among the preferred aryl groups are included, phenyl, tolyl, p-methoxyphenyl and p-ethoxyphenyl. In a particularly preferred aspect of this invention, $R^1$, $R^2$ and $R^3$ each are phenyl. The anion denoted by $X^{n-}$ can be, for example, a halide anion, the hydrogen sulphate anion, the perchlorate anion, the phosphate anion, the nitrate anion or a sulfonate anion. The anion is preferably either a halide anion, especially the chloride anion, or a hydrogen sulfate anion.

The term lower alkyl denotes both straight chain and branched chain saturated hydrocarbon groups containing from 1 to 7 carbon atoms such as methyl, ethyl, propyl, isopropyl, n-benzyl, etc. The term "lower alkoxy" denotes lower alkoxy groups containing from 1 to 7 carbon atoms such as methoxy, ethoxy, isopropoxy, etc. The term lower alkanoic acid designates monocarboxylic acids of aliphatic hydrocarbons containing from 1 to 7 carbon atoms such as formic acid, propionic acid, acetic acid etc.

The present process is advantageously carried out in the presence of an organic solvent in which the aforementioned 9-trans-beta-ionylidenethyltriarylphosphonium salt is at least slightly soluble. Any conventional inert organic solvent in which this salt is at least slightly soluble can be utilized in the process of this invention. Examples of such organic solvents are lower alkanoic acid, lower alkyl esters (e.g., methyl acetate, ethyl acetate, isopropyl acetate, etc.), aromatic hydrocarbons (e.g., toluene, xylene, etc.) and halogenated aliphatic hydrocarbons (e.g., trichloroethylene, 1,1,1-trichloroethane, tetrachloroethylene, etc.). Mixtures of such organic solvents can also be used. The organic solvents can contain traces of water which will not adversely affect the isomerization process. However, increasingly higher levels of water in the organic solvents can cause a corresponding increase in decomposition of the beta-ionylidenethyltriarylphosphonium salt during the isomerization. The preferred organic solvents are anhydrous solvents or solvents containing at most a trace amount of water. Among the preferred solvents are ethyl acetate, isopropyl acetate, toluene, xylene and tetrachloroethylene.

The process can be carried out at any temperature between 50° C. and 200° C. For optimum results, the temperature at which the present process is carried out depends on the particular organic solvent used. In a preferred embodiment of the process, which involves the use of ethyl acetate, isopropyl acetate, toluene, xylene or tetrachloroethylene as the organic solvent, the process is preferably carried out at a temperature of from about 50° C. to about 140° C. and especially at about 70° C. to 90° C. and more especially at about 80° C. The temperature chosen should, of course, be below that at which decomposition of the 9-cis- or 9-trans-beta-ionylidenethyltriarylphosphonium salt occurs.

The reaction can be carried out advantageously by heating for a period of at least 2 hours. For best results, the time required will vary according to the particular 9-cis-beta-ionylidenethyltriarylphosphonium salt used, the nature of the organic solvent, the temperature etc. In general, the process is completed in about 2-8 hours. However, the reaction can be carried out for periods at longer than 8 hours without any deleterious results. In view of the fact that no additional beneficial results are achieved by heating for such long periods, i.e., over 8 hours, these long periods are seldom used.

The present process is advantageously carried out at atmospheric pressure, although it may be carried out under pressure if desired. The process may also, if desired, be carried out under the atmosphere of an inert gas, such as nitrogen or argon if desired.

The process of this invention can convert the pure 9-cis compound of formula I to the corresponding 9-trans compound of formula II. The process of this invention can also be applied to isomerize mixtures which contain small amounts of the 9-cis compound of formula I in admixture with 9-trans-compound of formula II to increase the 9-trans content of the mixture. Any mixture or the 9-cis and 9-trans-beta-ionylideneethyltriarylphosphonium salts can be isomerized in accordance with this invention. The preferred mixtures for use in this invention are those which the 9-trans and 9-cis isomers are present in a ratio by weight of about 1:1 or those mixtures where the 9-cis isomer predominates.

The 9-trans-beta-ionylidenethyltriarylphosphonium salts of formula II are valuable intermediates in the synthesis of polyene compounds of the vitamin-A and carotenoid series having the trans-configuration in the 9-position. The present process enables such polyene compounds to be prepared in a more efficient manner than hitherto.

The following Examples illustrative but not limitative of the present invention. The ether in the Examples is diethyl ether.

EXAMPLE 1

A mixture containing 30.0 g. of 9-cis- and 9-trans-beta-ionylidenethyltriphenylphosphonium chloride in the approximate ratio of 1:1 by weight and 150 ml. of ethyl acetate was placed in a 500 ml. four-necked flask fitted with a stirrer, thermometer, reflux condenser and nitrogen inlet tube. A stream of nitrogen was passed over the mixture and the temperature was raised to 78° C. The mixture was stirred and heated at 78° C. for 5 hours.

The mixture was transferred to a 1 liter flask and the ethyl acetate was removed by evaporation at 40° C./10 mmHg. to leave a yellow oil. This was extracted with ether to remove impurities and gave 28.8 g. of mixture (96% return) containing 9-cis-beta-ionylidenethyltriphenylphosphonium chloride and 9-trans-beta-ionylidenethyltriphenylphosphonium chloride in the ratio by weight of 1:4 as determined by high-performance liquid chromatography (hplc).

EXAMPLE 2

The procedure described in Example 1 was repeated using toluene in place of ethyl acetate and using a temperature of 80° C. There were obtained 24.3 g. of a mixture (81% return) containing 9-cis-beta-ionylidenethyltriphenylphosphonium chloride and 9-trans-beta-ionylidenethyltriphenylphosphonium chloride in the ratio by weight of 1:7.7 as determined by hplc.

EXAMPLE 3

The same mixture containing 30.0 g. of 9-cis- and 9-trans-beta-ionylidenethyltriphenylphosphonium chloride as used in Example 1 and 300 ml. of isopropyl acetate were placed in a 500 ml. four-necked flask fitted with a stirrer, thermometer, reflux condenser and nitrogen inlet tube. A stream of nitrogen was passed over the mixture and the temperature was raised to 80° C. The mixture was stirred and heated at 80° C. for 5 hours. The mixture was then treated as described in Example 1 and gave 24.4 g. of a mixture (81% return) containing 9-cis-beta-ionylidenethyltriphenylphosphonium chloride and 9-trans-beta-ionylidenethyltriphenylphosphonium chloride in the ratio by weight of 1:5.4 as determined by hplc.

EXAMPLE 4

The procedure described in Example 3 was repeated using toluene in place of isopropyl acetate and using a temperature of 100° C. There were obtained 26.3 g. of a mixture (87% return) containing 9-cis-beta-ionylidenethyltriphenylphosphonium chloride and 9-trans-beta-ionylidenethyltriphenylphosphonium chloride in the ratio by weight of 1:6.6 as determined by hplc.

EXAMPLE 5

The procedure described in Example 3 was repeated using xylene in place of isopropyl acetate and using a temperature of 90° C. There were obtained 25.1 g. of a mixture (83% return) containing 9-cis-beta-ionylidenethyltriphenylphosphonium chloride and 9-trans-beta-ionylidenethyltriphenylphosphonium chloride in the ratio by weight of 1:7.1 as determined by hplc.

EXAMPLE 6

The procedure described in Example 3 was repeated using tetrachloroethylene in place of isopropyl acetate and using a temperature of 121° C. There were obtained 27.0 g. of a mixture (90% return) containing 9-cis-beta-ionylidenethyltriphenylphosphonium chloride and 9-trans-beta-ionylidenethyltriphenylphosphonium chloride in the ratio by weight of 1:4.1 as determined by hplc.

EXAMPLE 7

A mixture containing 20.0 g. of 9-cis- and 9-trans-beta-ionylidenethyltriphenylphosphonium hydrogen sulphate in the approximate ratio of 1:1.3 by weight and 100 ml. of toluene were placed in a 500 ml. four-necked flask fitted with a stirrer, thermometer, reflux condenser and nitrogen inlet tube. A stream of nitrogen was passed over the mixture and the temperature was raised to 80° C. The mixture was stirred and heated at 80° C. for 2 hours.

The mixture was then treated as described in the second paragraph of Example 1 and gave 19.1 g. of a mixture (95% return) containing 9-cis-beta-ionylidenethyltriphenylphosphonium hydrogen sulphate and 9-trans-beta-ionylidenethyltriphenylphosphonium hydrogen sulphate in the ratio by weight of 1:5.4 as determined by hplc.

EXAMPLE 8

The procedure described in Example 7 was repeated at a temperature of 100° C. There were obtained 18.2 g. of a mixture (91% return) containing 9-cis-beta-ionylidenethyltriphenylphosphonium hydrogen sulphate and 9-trans-beta-ionylidenethyltriphenylphosphonium hydrogen sulphate in the ratio by weight of 1:6.1 as determined by hplc.

EXAMPLE 9

A mixture containing 9-cis- and 9-trans-beta-ionylidenethyltriphenylphosphonium perchlorate in the ratio of 1:0.9 by weight and five volumes of toluene was stirred and heated at 80° C. for 5 hours in a similar manner to that described in Example 3. This gave a mixture (approximately 90% return) containing 9-cis-beta-ionylidenethyltriphenylphosphonium perchlorate and 9-trans-beta-ionylidenethyltriphenylphosphonium perchlorate in the ratio by weight of 1:2.8 as determined by hplc.

EXAMPLE 10

The procedure described in Example 9 was repeated using ethyl acetate in place of toluene and using a temperature of 78° C. There was obtained a mixture (approximately 90% return) containing 9-cis-beta-ionylidenethyltriphenylphosphonium perchlorate and 9-trans-beta-ionylidenethyltriphenylphosphonium perchlorate in the ratio by weight of 1:1.5 as determined by hplc.

EXAMPLE 11

The procedure described in Example 9 was repeated using a mixture containing 9-cis- and 9-trans-betaionylidenethyltriphenylphosphonium iodide in the ratio of 1:0.9 by weight in place of the mixture containing 9-cis- and 9-trans-beta-ionylideneethyltriphenylphosphonium perchlorate. There was obtained a mixture (approximately 90% return) of 9-cis-beta-ionylidenethyltriphenylphosphonium iodide and 9-trans-beta-ionylidenethyltriphenylphosphonium iodide in the ratio by weight of 1:2.3 as determined by hplc.

EXAMPLE 12

The procedure described in Example 11 was repeated using ethyl acetate in place of toluene and using a temperature of 78° C. There was obtained a mixture (approximately 90% return) of 9-cis-beta-ionylidenethyltriphenylphosphonium iodide and 9-trans-beta-ionylidenethyltriphenylphosphonium iodide in the ratio by weight of 1:1.7 as determined by hplc.

EXAMPLE 13

The procedure described in Example 9 was repeated using a mixture containing 9-cis- and 9-trans-beta-ionylidenethyltriphenylphosphonium bromide in the ratio of 1:0.9 by weight in place of the mixture containing 9-cis- and 9-trans-beta-ionylidenethyltriphenylphosphonium perchlorate. There was obtained a mixture (approximately 90% return) of 9-cis-beta-ionylidenethyltriphenylphosphonium bromide and 9-trans-beta-ionylidenethyltriphenylphosphonium bromide in the ratio by weight of 1:4.9 as determined by hplc.

EXAMPLE 14

The procedure described in Example 13 was repeated using ethyl acetate in place of toluene and using a temperature of 78° C. There was obtained a mixture (approximately 90% return) of 9-cis-beta-ionylidenethyltriphenylphosphonium bromide and 9-trans-beta-ionylidenethyltriphenylphosphonium bromide in the ratio by weight of 1:3.5 as determined by hplc.

EXAMPLE 15

The procedure described in Example 9 was repeated using amixture containing 9-cis- and 9-trans-beta-ionylidenethyltriphenylphosphonium nitrate in the ratio of 1:0.7 by weight in place of the mixture containing 9-cis- and 9-trans-beta-ionylidenethyltriphenylphosphonium perchlorate. There was obtained a mixture (approximately 90% return) of 9-cis-beta-ionylidenethyltriphenylphosphonium nitrate and 9-trans-beta-ionylidenethyltriphenylphosphonium nitrate in the ratio by weight of 1:3.6 as determined by hplc.

EXAMPLE 16

The procedure described in Example 15 was repeated using ethyl acetate in place of toluene and using a temperature of 78° C. There was obtained a mixture (approximately 90% return) of 9-cis-beta-ionylidenethyltriphenylphosphonium nitrate and 9-trans-beta-ionylidenethyltriphosphonium nitrate in the ratio by weight of 1:1.3 as determined by hplc.

EXAMPLE 17

The procedure described in Example 9 was repeated using a mixture containing 9-cis- and 9-trans-beta-ionylidenethyltriphenylphosphonium phosphate in the ratio of 1:0.7 by weight in place of the mixture containing 9-cis- and 9-trans-beta-ionylidenethyltriphenylphosphonium perchlorate. There was obtained a mixture (approximately 90% return) of 9-cis-beta-ionylidenethyltriphenylphosphonium phosphate and 9-trans-beta-ionylidenethyltriphenylphosphonium phosphate in the ratio by weight of 1:5.6 as determined by hplc.

EXAMPLE 18

The procedure described in Example 17 was repeated using ethyl acetate in place of toluene and using a temperature of 78° C. There was obtained a mixture (approximately 90% return) of 9-cis-beta-ionylidenethyltriphenylphosphonium phosphate and 9-trans-beta-ionylidenethyltriphenylphosphonium phosphate in the ratio by weight of 1:4.2 as determined by hplc.

EXAMPLE 19

The procedure described in Example 2 was repeated using toluene containing water (0.04% wt/vol). There was obtained a mixture (96% return) of 9-cis-beta-ionylidenethyltriphenylphosphonium chloride and 9-trans-beta-ionylidenethyltriphenylphosphonium chloride in the ratio by weight o 1:3.6 as determined by hplc.

EXAMPLE 20

The procedure described in Example 1 was repeated using ethyl acetate containing water (2.80% wt/vol). There was obtained a mixture (91% return) of 9-cis-beta-ionylidenethyltriphenylphosphonium chloride and 9-trans-beta-ionylidenethyltriphenylphosphonium chloride in the ratio by weight of 1:3.7 as determined by hplc.

EXAMPLE 21

A mixture containing 10.0 g. of 9-cis- and 9-trans-beta-ionylidenethyltriphenylphosphonium phosphate in the ratio of 1:0.6 and 100 ml. of methyl acetate containing water (8.10% wt/vol) was placed in a steel autoclave and sealed under an atmosphere of nitrogen. The autoclave was heated at 100° C. for 8.25 hours.

The mixture was then treated as described in Example 1 and gave 5.9 g. of a mixture (59% return) containing 9-cis-beta-ionylidenethyltriphenylphosphonium phosphate and 9-trans-beta-ionylidenethyltriphenylphosphonium phosphate in the ratio by weight of 1:3.7 as determined by hplc.

I claim:

1. A process for the isomerization of a composition containing 9-cis-beta-ionylidenethyltriarylphosphonium salt of the formula

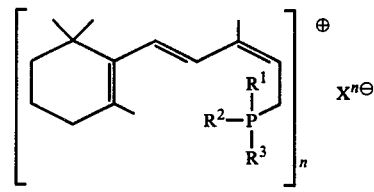

wherein $R^1$, $R^2$ and $R^3$ each is aryl, $X^{n\ominus}$ is an anion of a strong acid and n is 1, 2 or 3, to a corresponding 9-trans-beta-ionylidenethyltriarylphosphonium salt of the formula

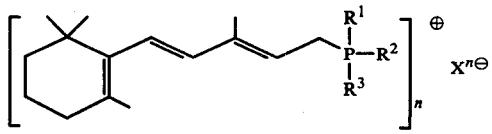

wherein n, $R^1$, $R^2$, $R^3$ and $X^{n\ominus}$ are as above, comprising heating to a temperature of from 50° C to 200° C said 9-cis-beta-ionylidenethyltriarylphosphonium salt in the presence of an organic solvent.

2. A process of claim 1, wherein $R^1$, $R^2$ and $R^3$ are each a phenyl.

3. The process of claim 1, wherein $X^{n\ominus}$ is a halide anion, the hydrogen sulphate anion, the perchlorate anion, the phosphate anion, the nitrate anion or a sulphonate anion.

4. The process of claim 3, wherein $X^{n\ominus}$ is a halide or hydrogen sulphate anion.

5. The process of claim 4, wherein said halide anion is the chloride anion.

6. The process of claim 1, wherein the organic solvent is one in which 9-trans-beta-ionylidenethyltriarylphosphonium salt is at least slightly soluble.

7. The process of claim 6, wherein the organic solvent is a lower alkanoic acid lower alkyl ester, an aromatic hydrocarbon or a halogenated aliphatic hydrocarbon.

8. The process of claim 7, wherein the organic solvent is ethyl acetate, isopropyl acetate, toluene, xylene or tetrachloroethylene.

9. The process of claim 8, hwerein heating is carried out at a temperature of from about 50° C. to 140° C.

10. The process of claim 9, wherein heating is carried out at a temperature of from about 70° C. to 90° C.

11. The process of claim 10, wherein the heating is carried at about 80° C.

12. The process of claim 1, wherein the composition contains a mixture of 9-cis- and 9-trans-beta-ionylidenethyltriarylphosphonium salts in which the 9-cis-and 9-trans- isomers are present in a ratio by weight of approximately 1:1 or in which the 9-cis-isomer predominates.

* * * * *